(12) United States Patent
Petyaev

(10) Patent No.: US 9,517,214 B2
(45) Date of Patent: Dec. 13, 2016

(54) FAT-BASED FOOD PRODUCTS

(71) Applicant: IP Science Limited, Cambridge (GB)

(72) Inventor: Ivan Petyaev, Cambridge (GB)

(73) Assignee: IP Science Limited, Cambridge (GB)

( * ) Notice: Subject to any disclaimer, the term of this patent is extended or adjusted under 35 U.S.C. 154(b) by 0 days.

(21) Appl. No.: 14/365,051

(22) PCT Filed: Dec. 13, 2012

(86) PCT No.: PCT/GB2012/053126
§ 371 (c)(1),
(2) Date: Jun. 12, 2014

(87) PCT Pub. No.: WO2013/088156
PCT Pub. Date: Jun. 20, 2013

(65) Prior Publication Data
US 2015/0004268 A1    Jan. 1, 2015

(30) Foreign Application Priority Data
Dec. 14, 2011  (GB) ................... 1121519.1

(51) Int. Cl.
| | |
|---|---|
| A01N 65/00 | (2009.01) |
| A61K 31/01 | (2006.01) |
| A23C 9/152 | (2006.01) |
| A23D 7/005 | (2006.01) |
| A23L 2/58 | (2006.01) |
| A23D 9/007 | (2006.01) |
| A21D 2/14 | (2006.01) |
| A21D 2/16 | (2006.01) |
| A23C 9/13 | (2006.01) |
| A23C 15/12 | (2006.01) |
| A23L 1/30 | (2006.01) |
| A61K 8/31 | (2006.01) |
| A61K 36/81 | (2006.01) |

(52) U.S. Cl.
CPC ............ *A61K 31/01* (2013.01); *A21D 2/14* (2013.01); *A21D 2/165* (2013.01); *A23C 9/1307* (2013.01); *A23C 9/152* (2013.01); *A23C 15/12* (2013.01); *A23D 7/0053* (2013.01); *A23D 7/0056* (2013.01); *A23D 9/007* (2013.01); *A23L 1/30* (2013.01); *A23L 2/58* (2013.01); *A61K 8/31* (2013.01); *A61K 36/81* (2013.01); *A23V 2002/00* (2013.01); *A61K 2800/82* (2013.01)

(58) Field of Classification Search
CPC ..................................... A61K 36/00
USPC ....................................... 424/725
See application file for complete search history.

(56) References Cited

U.S. PATENT DOCUMENTS

| | | |
|---|---|---|
| 6,262,109 B1 | 7/2001 | Clark et al. |
| 2007/0122509 A1 | 5/2007 | Chomczynski |
| 2009/0239945 A1 | 9/2009 | Casey et al. |
| 2009/0318567 A1 | 12/2009 | Petyaev et al. |
| 2011/0182930 A1* | 7/2011 | Erlanson-Albertsson  A61K 36/02 424/195.17 |

FOREIGN PATENT DOCUMENTS

| | | |
|---|---|---|
| WO | WO-03/017785 A1 | 3/2003 |
| WO | WO-2006/046222 A2 | 5/2006 |

OTHER PUBLICATIONS

Agarwal et al, "Lycopene Content of Tomato Products: Its Stability Bioavailability and In Vivo Antioxidant Properties", Journal of Medicinal Food vol. 4, No. 1, 2001, pp. 9-15.
Ballantyne et al, "Lipids and CVD management towards a global consensus", European Heart Journal 26, 2005, pp. 2224-2231.
Engelhard et al, "Natural antioxidants from tomato extract reduce blood pressure in patients with grade-1 hypertension: A double-blind study, placebo-controlled pilot study" American Heart Journal vol. 151, Jan. 2006, pp. 100.e1-100.e6.
Hak, et al, "Prospective Study of Plasma Carotenoids and Tocopherols in Relation to Risk of Ischemic Stroke", Stroken No. 35, 2004, pp. 1584-1588.
Kiokias et al, "Dietary supplementation with a natural carotenoid mixture decreases oxidative stress", European Journal of Clinical Nutrition, No. 57, 2003, pp. 1135-1140.
Klipstein-Grobusch et al, "Serum carotenoids and atherosclerosis the Rotterdam Study", Atherosclerosis, No. 148, 2000, pp. 49-56.
Kohlmeier et al, "Lycopene and Myocardial Infraction Risk in the EURAMIC Study", American Journal of Epidemiology, vol. 146. 1997, pp. 618-626.
Leal-Calderon et al, "Emulsified Lipids: formulation and control of end-use properties", Dossier-Fonctionnalites Des Hulles, vol. 19(2), 2012, pp. 111-119.
Meagher et al, "Addressing Cardiovascular Disease in Women: Focus on Dyslipidemia", JABFP vol. 17, No. 6, 2004, pp. 424-437.
Misra et al, "LycoRed as an alternative to hormone replacement therapy in lowering serum lipids and oxidative stress markers: A randomized controlled clinical trial", (2005) Japan Society of Obstetrics and Gynecology Res., vol. 32, No. 3, Jun. 2006, pp. 299-304.

(Continued)

*Primary Examiner* — Michael Meller
(74) *Attorney, Agent, or Firm* — Norton Rose Fulbright US LLP

(57) ABSTRACT

The invention is in particular concerned with a food product comprising one or more fats or oils and a carotenoid compound. The products of the invention may be used in reducing elevated total cholesterol, triglycerides and inflammatory damage, as well as improving tissue microcirculation and tissue oxygenation.

6 Claims, No Drawings

(56) References Cited

OTHER PUBLICATIONS

Palozza et al, "Lycopene in atherosclerosis prevention an integrated scheme of the potential mechanisms of action from cell culture studies", Archives of Biochemistry and Biophysics, No. 504, 2010, pp. 26-33.
Paterson et al, "Supplementation with Fruit and Vegetable Soups and Beverages Increases Plasma Carotenoid Concentrations but Does Not Alter Markers of Oxidative Stress of Cardiovascular Risk Factors", The Journal of Nutrition, No. 136, 2006, pp. 2849-2855.
Rao et al, "Carotenoids and Human Health", Pharmacological Research, No. 55. 2007. pp. 207-216.
Reid et al, "Protective effect of lycopene on serum cholesterol and blood pressure: Meta-analyses of intervention trials", Maturitas, No. 68, 2011, pp. 299-310.
Rissanen et al, "Low serum lycopene concentration is associated with an excess incidence of acute coronary events and stroke: the Kuopio Ischaemic Heart Disease Risk Factor Study", British Journal of Nutrition, No. 85, 2001, pp. 749-754.
Rissanen et al, Serum Lycopene Concentrations and Carotid Atherosclerosis: the Kuopio Ischaemic Heart Disease Risk Factor Study. The American Journal of Clinical Nutrition, No. 77, 2003, pp. 133-138.
Sakamoto et al, "*Elevation of Serum Carotenoids after Continual Ingestion of Tomato Juice*", Japan Society of Nutrition Food Science, vol. 47, 1994, pp. 93-99.
Sesso et al, "Dietary Lycopene, Tomato-Based Food Products and Cardiovascular Disease in Women", American Society for Nutritional Science. No. 133, 2003, pp. 2336-2341.
Sesso et al, "Plasma lycopene, other carotenoids and retinol and the risk of Cardiovascular Disease in Men", The American Journal of Clinical Nutrition, No. 81, 2005, pp. 990-997.
Shen et al, "Contibution of Tomato Phenolics to Antioxidation and Down-Regulation of Blood Lipids", Journal of Agricultural and Food Chemistry, No. 55, 2007, pp. 6475-6481.
Silaste, et al, "Tomato juice decreases LDL cholesterol leves and increases LDL resistance to oxidation", British Journal of Nutrition, No. 98, 2007, pp. 1251-1258.
Steinberg et al, "An Interpretive history of the cholesterol controversy: part II: the early evidence linking hypercholesterolemia to coronary disease in humans", Journal of Lipid Research. vol. 46, 2005, pp. 179-190.
Zaripheh et al, "The Biodistribution of a Single Oral Dose of [$^{14}$C]-Lycopene in Rats Prefed Either a Control or Lycopene-Enriched Diet", The Journal of Nutrition, No. 135, 2005, pp. 2212-2218.

\* cited by examiner

FAT-BASED FOOD PRODUCTS

CROSS REFERENCE TO RELATED APPLICATIONS

This application is a national phase application under 35 U.S.C. §371 that claims priority to PCT Application No. PCT/GB2012/053126 filed on Dec. 13, 2012, which claims the benefit of Great Britain Application No. 1121519.1 filed Dec. 14, 2011, both of which applications are incorporated by reference herein in their entirety.

FIELD OF THE INVENTION

This invention relates to fat-based food products, such as butter and margarine, and in particular to formulations of fat-based food products which have beneficial effects on parameters of metabolism in individuals including levels of triglycerides, cholesterol and other lipids, molecular oxygen transport and its metabolism, oxygen tissue saturation, control of hypoxia/ischaemia, as well as markers of inflammation and inflammatory oxidative damage.

BACKGROUND OF THE INVENTION

Butter and other food products containing fats, such as dairy or other animal, bird or plant fats, are the staple part of traditional diets of many nations around the globe. On the one hand they provide humans, and some domesticated animals, with the source of energy and other essential nutrients, on the other hand their overconsumption results in increase of their blood lipids [for example B. Bronte-Stewart, British Medical Bulletin, v. 14, 3: 243-252; M. B. Katan, P. L. Zock, and R. P. Mensink Am J. Cli., Nutr 1994; 60 (suppl):1O17S-22S]. There are many different types of animal, bird and plant fats and food products based on them, including butter, milk, dairy cream; lard; pork, beef, camel, goat; beef, mutton, goat and camel tallow; goat and camel fat; eggs, goose, duck and other poultry fat; liver pates; margarines, shortenings; coconut, palm and menhaden oils, and many products.

Consumption of fat containing products by humans results in increases in blood lipids and their overconsumption is one of the main dietary sources responsible for development of hyperlipidaemias, overload and inefficiency of lipid metabolism, which eventually lead to individuals becoming overweight and obesity, and epidemic spread of Metabolic Syndrome, Atherosclerosis and their clinical complications, such as Diabetes II and Cardio-Vascular Diseases (CVD).

It is difficult to overestimate the importance of the nutritional education, government policies, public awareness and food industry regulations to reduce overconsumption of fats in our diets. The introduction of new alternative substitutes for animal fat products for human consumption based on plant stanol esters has important but limited effect on the overall situation. The main reason is that human dietary tastes are formed in childhood and are very difficult to change in adults. Therefore, one of the main conditions for the success of the introduction of any potential new ways of food modulating technologies is its ability to achieve nutritional targets without changes in the taste and other basic properties of the consuming products.

Lycopene is known to be a potent antioxidant. Although 25 mg of lycopene and above is considered to be safe for certain periods of administration, it is far above the daily level which could be consumed with a diet rich with tomato or tomato processed products (about 6-10 mg). Daily consumption of 6-10 mg lycopene has been reported to have no effect on cholesterol or other blood lipids [Bose et al Singapore Med J 2007; 48 (5): 415-420; Upritchard et al Diabetes Care, 2000, 23 6: 733-735].

SUMMARY OF THE INVENTION

This invention relates to the finding that incorporating carotenoid compounds into food products which contain fats, such as animal fats and vegetable oils, causes these food products to exert a positive effect on levels of triglycerides, cholesterol, LDL, and other metabolic parameters in individuals, despite being rich in saturated and unsaturated fats.

An aspect of the invention provides a food product which comprises one or more fats or oils and a carotenoid compound. Preferably the carotenoid compound is an isolated carotenoid compound.

The invention therefore provides a food product comprising one or more fats or oils and a carotenoid compound.

The invention additionally provides a food product of the invention for use in:

(a) reducing elevated levels of cholesterol, LDL and/or triglyceride in an individual;

(b) reducing subclinical or clinical inflammation; reducing anti-inflammatory oxidative damage; increasing plasma molecular oxygen transport, microcirculation and tissue oxygen saturation, reducing already developed liver (micro-) damage and liver steatosis, liver and other organs, including peripheral, tissue hypoxia or ischaemia; increasing antioxidant activity and/or reducing or delaying symptoms of aging in an individual; and/or (c) reducing postprandial cholesterol- and triglyceride-aemias, reducing size of chylomicrons and increasing rate of their clearance, reducing postprandial inflammatory and oxidative stress, reducing postprandial or other liver (micro-damage and liver steatosis, liver and other organs, including peripheral tissue hypoxia or ischaemia, or delaying of above mentioned symptoms of fat, or excessive, or imbalance food intake in an individual.

The invention further provides a food product of the invention for use in the nutrition of an individual, preferably for use in the nutrition of the individual to treat one of the conditions referred to herein.

The invention further provides a method of:

(a) improving the appearance of an individual comprising administering a nutracosmetic formulation of the invention to the individual; and/or (b) reducing or delaying visible signs of aging and performance in an individual comprising administering a nutracosmetic formulation of the invention to the individual.

The invention additionally provides a method of:

(a) reducing elevated levels of cholesterol, LDL and/or triglyceride in the blood of an individual comprising administering a food product of the invention to an individual in need thereof (b) reducing subclinical or clinical inflammation; reducing anti-inflammatory oxidative damage; increasing plasma molecular oxygen transport, microcirculation and tissue oxygen saturation, reducing already developed liver (micro-) damage and liver steatosis, liver and other organs, including peripheral, tissue hypoxia or ischaemia; increasing antioxidant activity and/or reducing or delaying symptoms of ageing in an individual; comprising administering a food product according of the invention to an individual in need thereof.

(c) reducing postprandial cholesterol- and triglyceride-aemias, reducing size of chylomicrons and increasing rate of their clearance, reducing postprandial inflammatory and oxidative stress, reducing postprandial or other liver (micro-damage and liver steatosis, liver and other organs, including peripheral tissue hypoxia or ischaemia, or delaying of above mentioned symptoms of fat, or excessive, or imbalance food intake in an individual; comprising administering a food product of the invention to an individual in need thereof;

(d) providing nutrition to an individual comprising administering a food product of the invention to an individual in need thereof; and/or (e) slimming, weight reduction or dieting comprising administering a food product of the invention.

The invention also provides a method of producing a food product which comprises adding a carotenoid compound during production of the food product, so producing a food product of the invention.

The invention further provides a butter, lard, margarine, or oil comprising a carotenoid compound, preferably an isolated carotenoid compound.

DETAILED DESCRIPTION OF THE INVENTION

The food product of the invention may comprise a homogenous matrix which contains the fats and the carotenoid compound. For example, the fats and carotenoid compound may be blended together in a food matrix. Fats may comprise one or more fat compounds. Fat compounds may include phospholipids, cholesterol and triglycerides (i.e. triesters of glycerol and fatty acids).

A fat compound may comprise saturated fatty acids ($C_nH_{(2n+1)}CO_2H$ where n is typically 13 to 17), such as palmitic acid, myristic acid and stearic acid and/or unsaturated fat compounds, such as oleic acid, palmitoleic acid, linoleic acid and linolenic acid. The fats may comprise, for instance, medium or long chain triglycerides.

Unsaturated fatty acids may be mono-unsaturated ($C_nH_{(2n-1)}CO_2H$) or poly-unsaturated (e.g. $CnH_{(2n-3)}CO_2H$ and $C_nH_{(2n-5)}CO_2H$). Unsaturated fatty acids may include cis or trans isomers.

As described above, fatty acids may be esterified and typically exist in fats as triglycerides.

Fats used in food products typically comprise a mixture of different fat compounds. For example, a fat may comprise 10% to 80% by weight saturated fat, 10% to 80% by weight monounsaturated fat and/or 1% to 80% by weight polyunsaturated fat. In some instances the amount of saturated fat, monosaturated fat and/or polyunsaturated fat may be from 5 to 100% by weight, from 10 to 90% by weight, from 20 to 80% by weight or from 30 to 70% by weight, such as from 40 to 60% by weight. In some cases, the amount of saturated fat, monosaturated fat and/or polyunsaturated fat may be up to 99%, 98%, 97%, 96%, 95% or 85% by weight or at least those values. The amount by weight may be in a range whose endpoints are defined by any two of the above values. The total amount of fat may be in any of the above specified amounts or ranges.

Suitable fats for use in food products are well known in the art and encompassed by the invention and include cooking or dietary oils, fats and lipids obtained from animals, plants or other sources.

Animal fats may include butterfat; lard; fish oil; blubber (e.g. whale blubber); pork; beef; mutton; camel; goat; beef, mutton, goat or camel tallow; beef, mutton, goat or camel fat, suet or dripping; eggs; goose, duck and other poultry fat; and liver pate. Other suitable animal fats are well known in the art. Animal fats may be obtained from dairy products or from the tissues of mammals, fish or poultry, for example using commercial rendering or extraction processes. In one instance, the food product may be, or comprise, rendered fat. The food product may be, for instance, a dairy or non-dairy product.

In some embodiments, the fat may be butterfat, which is derived from milk or cream. The food product of the invention may be a milk, typically a full fat milk, or a cream, such as a double or whipping cream or may be a food product comprising such milk or cream. The invention also provides milk and cream substitutes. The food product may be, for instance, a cake comprising such cream, milk, or substitutes.

In one instance, the invention provides butter comprising the carotenoid, as well as lard, dripping, goose fat, beef fat or other popular animal fats comprising the carotenoid. A pat or block of such animal fat, particularly butter, is provided. The product of the invention may be a block of cooking fat, or in some instances a bottle, drum or any suitable container of cooking oil. In one preferred instance, the invention provides a butter, margarine or other spread comprising any of the amounts of carotenoid specified herein, preferably from 0.05 to 1 mg per gram of the product, more preferably from 0.1 to 5 mg of carotenoid per gram of the product and even more preferably from 0.1 to 0.3 mg carotenoid per gram of the product In one preferred instance, the butter, margarine or other spread provides about 4 to 10 mg carotenoid, preferably 5 to 8 mg of carotenoid and in particular about 7 mg of carotenoid per 30 g serving. In one particularly preferred instance, the food product is butter and/or the carotenoid is lycopene, preferably provided via incorporation of oeloresin into the butter.

The food product of the invention may be hydrogenated or non-hydrogenated, but in one preferred instance is hydrogenated. The food product of the invention may be, or comprise, shortening. Shortening typically helps prevent cross-linking between gluten molecules. Typically shortening will comprise a hydrogenated vegetable oil, the oil may be, for instance, any of the types of oil mentioned herein. For instance, the shortening may comprise, or be made from, cottonseed oil, corn oil, and soy beans, in one instance being a blend of soybean and palm oils. The invention also provides a foodstuff comprising such shortening, such as a baked product and in particular pastry.

The food product of the invention may have a weight, for instance, of about 50 g, 200 g, 250 g, 300 g, 400 g, 454 g, 500 g, 750 g, 1 kg, 5 kg, 10 kg or more or an amount in a range whose endpoints are defined by any of those two values. In some instances, where the product is an oil or other liquid, it may be, for instance, in an amount of about 200 ml, 250 ml, 500 ml, 750 ml, 1 liter, 5 liter, 10 liter, 50 liter or 100 liters or in a range with any two of those values as endpoints.

Vegetable fats include margarines and vegetable oils, such as palm oil, soybean oil, rapeseed oil, olive oil, peanut oil, ground nut oil, palm oil, sunflower oil, sesame oil, menhaden oil and coconut oil. Other suitable vegetable oils are well known in the art and such oils comprising a carotenoid are also provided. In one preferred instance, the oil is a vegetable oil or an olive oil.

In one preferred instance, the food product provided is an oil, in particular an edible oil and/or a cooking oil, particularly such vegetable oils. An edible oil is typically an oil that be directly consumed and/or used in cooking, particularly one which can be directly consumed. The food products of the invention are preferably editable. The oil of the invention may be a cooking oil, for instance one for use in frying food and/or for addition to food as an ingredient, particularly an oil for cooking. The food product of the invention may be a fat, particularly an edible fat and/or one for cooking, including any of those mentioned herein. A cooking fat is one which may be typically used as an ingredient for food, though may be melted and used to fry food.

In some embodiments, the fat in the food product is not cocoa-butter or other cocoa bean derived fat. In some instance, the food product of the invention is not, or does not comprise, chocolate. In other instances, it may comprise cocoa-butter, a cocoa bean derived fat or be chocolate.

In some embodiments, fats for incorporating into food products may be produced from natural sources by commercial processes, such as hydrogenation of naturally occurring fats.

A food product containing fat may contain at least 1% by weight, at least 10% by weight, at least 15% by weight, at least 20% by weight, at least 25% by weight or at least 30%, at least 40%, at least 50%, at least 60%, at least 70%, at least 80%, or at least 90% by weight of fat relative to the total weight of the product or a value in a range having any of those two values as endpoints. In one instance, the food product comprises 60 to 62% of fat and so in the case of a spread can represent "Three-quarter-fat margarine" or "reduced-fat margarine", in others the amount of fat may be about 39 to 41% of fat and so in the case of a spread may be called "half-fat margarine", "low-fat margarine" or "light margarine".

In one instance, the food product may be one considered to be a food product high in unsaturated fats, in another it may be a food product high in saturated fats. The food product may be one comprising trans fats, for instance it may be high in such fats, or be low in trans fats.

In some embodiments, a food product may further comprise non-fat ingredients, such as proteins, sugars and other compounds, in addition to fat compounds.

For the avoidance of doubt, aspects of the invention provide food products which comprise all combinations of the above parameters.

In some embodiments, the fat compounds may form a food matrix. The carotenoid compound may be incorporated into the food matrix by blending or admixing.

Any fat-based food product may be supplemented with a carotenoid compound as described herein. For example, the food product may be a foodstuff, a beverage or a dietary supplement or nutraceutical product.

Foodstuff products include bread, flour, shortening, cereal, biscuit, pastry, dairy products, such as cheese spread, cheese, cream and yoghurt, fillings, pastes, sauces and mousses. Other suitable foodstuffs are well known in the art. In one preferred instance, the foodstuff may be, or comprise, pastry, for example it may be a pie, flan, tart or cake comprising pastry. The pastry may be, for instance, a puff pastry or a filou pastry, it may be a pastry intended for use in pie casings, flan or tart bases and the like.

In some embodiments, the foodstuff may comprise butterfat, for example, the foodstuff may be, or comprise cheese, butter, milk, cream or ice cream. The food product of the invention may be a spreadable food, particularly a spreadable fat or food comprising a high level of fat. In one case, the foodstuff is a spread, such as a margarine or butter. The food product may be a spreadable cheese. The food product of the invention may be a cheese slice or cheese slice.

In other embodiments the foodstuff is margarine or lard or other cooking fat. The cooking fat may be a cooking margarine, it may be, for instance, a yellow or white cooking fat. Margarine is typically a semi-solid emulsion composed mainly of vegetable fats and water, particularly plant oils and fats. The margarine may, for instance, comprise water, citric acid, vitamins and/or milk powder. Emulsifiers such as lecithin may also be present. In one instance, the food product of the invention is a blend of margarine and butter and in particular is a spread comprising a blend of margarine and butter.

In one instance the margarine is a water-in-oil emulsion derived from vegetable/animal fats, with a fat content of at least 80%, but less than 90%, that remain solid at a temperature of 20° C. and is suitable as spread. In some instances, the margarine does not have a milk fat content of more than 3%. In other instances, particularly for blended spreads, the milk fat may be between 10% and 80%

A food product of the invention may comprise vitamins, particularly vitamins A and/or D.

In one instance, the food product of the invention may be, or comprise cheese. The cheese may be, for instance, a hard cheese or a soft cheese. For instance, it may be a cheddar, stilton, camembert, gouda, edam, Roquefort, mozzarella, parmesan or other cheese. In one preferred instance, the cheese is a cheddar cheese. The food product may be a cheese spread and/or processed cheese. In one instance, the cheese is a smoked cheese and in particular a smoked processed cheese. The food product may be a formed cheese product, such a cheese triangle or slice. The cheese may be a cheese spread. The cheese may be a hard or soft cheese. In further instances, the food product is, or comprises, a fungal cheese. In a preferred instance, the cheese is a blue or white fungal cheese. The cheese may be a veined cheese. Suitable cheeses include Roquefort; Camembert; Danish Blue cheese; Creamy Blue; Stilton; Cabrales, Blue Brie, Cambozola; Fourme d'Ambert; Gorgonzola; Bleu d'Auvergne and Cibosano and other mould containing cheeses.

The cheese may be, for instance, a cheese made from, or comprising, cow, sheep, goat or buffalo milk. The cheese may be pasteurised or unpasteurised. The cheese may have been subjected to UHT treatment. Any of the compositions discussed herein may have been pasteurised or UHT treated or may be unpasteurised.

In another instance, the food product may be a processed food. As well as processed cheese, the food product may be, or comprise, a processed meat. For instance, the food product may be, or comprise, a salami, sausage or pate. Such food products may comprise meat from any of the animals described herein, for instance, they may comprise, pork, beef, lamb or be from poultry, such as goose, duck or chicken.

Beverages may include any drink which comprises fat compounds and may include dairy and non-dairy drinks. Beverages may be non-alcoholic or alcoholic. The formulation of suitable beverages is well-known in the art. The beverage may be, or comprise, a dairy product, such as milk, butter or cream. In some instances it may be a milkshake. The food product of the invention may also be something for addition to a beverage, such as a cream or cream substitute, for instance in a single serving container.

A food product may, in some instances not itself be for direct consumption, but is something which may be incorporated into, or used in the preparation of, a foodstuff. For instance, the invention provides cooking oils and fats intended for food preparation. The invention also provides ingredients to be used in the preparation of a food-stuff, particularly fats or oils for such a purpose and cooking fats or margarines. The invention also provides a foodstuff cooked in a fat or oil of the invention, for example one fried in such a fat or oil. Examples of such foodstuffs include a chip or crisp so prepared. The food product of the invention may be a batter and the food stuffs discussed herein may be coated with such a batter. In one preferred instance, the invention further provides a foodstuff comprising a fat or oil of the invention.

Dietary supplements or nutraceutical products may be in any form suitable for oral administration (e.g., by ingestion) and may be presented as discrete units such as capsules, cachets or tablets; as a powder or granules; as a solution or suspension in an aqueous or non-aqueous liquid; or as an oil-in-water liquid emulsion or a water-in-oil liquid emulsion; as a bolus; as an electuary; or as a paste.

In some embodiments, a food product as described herein may lack cocoa solids, cocoa butter or other cocoa-bean products.

In addition to fat compounds, food products described herein comprise a carotenoid compound. In some preferred embodiments, the carotenoid compound may be isolated. An isolated carotenoid compound is outside the physical milieu or environment in which it occurs in nature. For example, an isolated carotenoid compound may be free or substantially free from its natural environment e.g. it is not contained in the natural plant material with which it is naturally associated. Isolated carotenoid compounds include compounds which have been isolated, concentrated, purified or partially purified from natural sources, such as plants, and compounds which have been produced synthetically. The carotenoid compound may be contained within a carotenoid-rich product, such as tomato or other plant paste, sauce, concentrate, oleoresin, fraction or extract.

The food product may comprise 0.0001% to 1%; 0.001% to 1%; or 0.01% to 0.1% by weight of carotenoid compound. For example, the food product may comprise 0.001 to 10 mg of carotenoid compound per one gram of food product, for example, 0.01 to 10 mg per gram or 0.1 to 1 mg per one gram of food product.

In some instances, the food product may be one enriched for the carotenoid, in other words one supplemented, augmented or enriched for the carotenoid, for instance, in comparison to the food-product normally. The amount of carotenoid may be, for instance, about 10%, 20%, 30%, 40%, 50%, 60%, 70%, 80%, 90%, 100% or more than the non-enriched form of the product or may have an increase in carotenoid in a range whose endpoints are defined by any two of those values. The enrichment may be, for instance, five, ten, fifteen, twenty, fifty fold or more compared to before addition of the carotenoid or a value in the range having any of those values as endpoints. The carotenoid may be one not normally found in the food-product or found in an amount less than 3, 2, 1, 0.5, 0.1, 0.05 mg, 0.01 mg in total, or per gram, of the food product.

The food product may be in a unit dose form which allows a controlled daily dose of carotenoid, in particular, lycopene to be consumed. For example, the food product may be formulated to provide a daily dose of 0.1 mg to 100 mg of carotenoid/lycopene, preferably 0.5 to 50 mg of carotenoid lycopene, for instance from 0.5 to 25 mg, 1.0 or 15 mg, 2.0 to 10 mg, 5 to 10 mg or in a range defined by any two of those values, the food product may be in some instances, in a unit dose form which allows a controlled daily dose of carotenoid, preferably lycopene, to be consumed. For example, the food product may be formulated to provide a daily dose of 0.1 mg to 100 mg of lycopene, preferably 0.5 to 50 mg of lycopene. In some instances, a product of the invention may provide about 0.1 mg, 0.2 mg, 0.5 mg, 1 mg, 1.5 mg, 2 mg, 2.5 mg or more of carotenoid such as about 3, 4, 5, 6, 7, 8, 9, or 10 mg of carotenoid and in particular those values of lycopene. The product may comprise an amount of carotenoid which is in a range with any two of the values mentioned herein as endpoints.

In one instance, the foodstuff or product provides from 0.1 to 1.0 mg of carotenoid per gram of foodstuffs for example at least 0.2, 0.3, 0.4 or 0.5 mg carotenoid per gram of foodstuff, with in some instances, up to 0.3, 0.4, 0.5, 0.6, 0.7, 0.8, 0.9 or 1.0 mg of carotenoid per gram of product. In another instance, the level of foodstuff administered is enough to reduce any of the makers discussed herein, preferably to near, or at, or below baseline levels for a healthy control or below baseline prior to administration of the product.

The fat or oil and carotenoid may be present in a synergistic amount. For instance, they may be present where the combination produces a greater effect on any of the parameters mentioned herein than either individually when provided in the same amount. The invention therefore also provides a synergistic combination of a fat or oil and carotenoid or any of the food products described herein may have such amounts.

Carotenoid compounds are tetraterpenoids which contain long polyene chains. Carotenoid compounds include xanthophylls such as lutein and zeaxanthin, and carotenes, such as beta-carotene, alpha-carotene, zeto-carotene, and lycopene compounds.

Lycopene compounds may include lycopene, 1-HO-3',4'-didehydrolycopene, 3,1'-(HO)$_2$-gamma-carotene, 1,1'-(HO)2-3,4,3',4'-tetradehydrolycopene, 1,1'-(HO)2-3,4-didehydrolycopene.

In preferred embodiments, the carotenoid compound is a lycopene compound preferably lycopene. Lycopene is an open-chain unsaturated $C_{40}$ carotenoid of structure I (Chemical Abstracts Service Registry Number 502-65-8).

Structure I

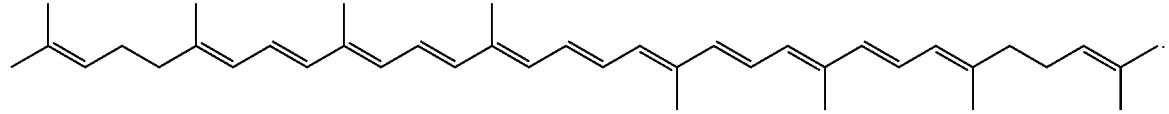

Lycopene occurs naturally in plants such as tomatoes, guava, rosehip, watermelon and pink grapefruit and any such sources of lycopene may be, for instance, employed.

Lycopene for use as described herein may comprise one or more different isomers. For example, lycopene may include cis-lycopene isomers, trans-lycopene isomers and mixtures of the cis- and trans-isomers. Lycopene may comprise at least 10%, at least 20%, at least 30%, at least 40%, at least 50%, at least 60%, at least 70%, at least 80%, at least 90%, or at least 95% (Z)-isomers, (all-E)-isomers, or cis-isomers, such as 5-cis- or 9-cis- or 13-cis-isomers, which have improved bioavailability relative to trans isomers. Trans isomers may isomerise into cis forms in vivo, or during storage and processing.

Carotenoid compounds, such as lycopene, for use as described herein may be natural i.e. obtained from a natural source, for example, extracted from a carotenoid-rich fruit, vegetable or other plant, such as a tomato or melon, or from fungi, algae or bacteria. In one instance, the carotenoid compound may be, or comprise, oleoresin, particularly tomato oleoresin.

In one instance, the carotenoids comprise medium or high length carbohydrate chains and/or the carotenoid has tropism and/or affinity for carotenoid receptors. In a further instance, the carotenoid may be incorporated into chylomicrone/lipoprotein. In particular, it may be that, for instance, the carotenoid is able to anchor lipoprotein/chylomycrone molecules to help deliver them to carotenoid receptors, particularly liver carotenoid receptors. In some cases the carotenoids are specific or have high affinity for carotenoid receptors, in other they may be semi-specific or have low affinity for carotenoid receptors. In one instance, it may be that, for instance, the Kd value for affinity that may be $10^{-5}$, $10^{-6}$, $10^{-7}$, $10^{-8}$ M or higher for the receptor.

A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed.

In some instances, the ratio of carotenoid to triglyceride or other fat molecules in the products of the invention may be from 1:1000 to 1:100,000, for instance from 1:2000 to 1:50,000, or from 1:5000 to 1:25,000.

Carotenoid compounds, such as lycopene, for use as described herein may be synthetic i.e. produced by artificial means, for example, by chemical synthesis. A range of methods for chemical synthesis of lycopene and other carotenoids are known in the art. For example, a three-stage chemical synthesis based on the standard Wittig olefination reaction scheme for carotenoid synthesis may be employed, in which an organic solution of $C_{15}$ phosphonium methanesulfonate in dichloromethane (DCM) and an organic solution of $C_{10}$ dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then be heated and cooled to crystalline slurry that is filtered and washed with methanol. The lycopene crystals may then be recrystallized and dried under heated nitrogen. Synthetic carotenoids, such as lycopene, are also available from commercial suppliers (e.g. BASF Corp, NJ USA).

Synthetic carotenoid compounds, such as lycopene, may comprise an increased proportion of cis isomers relative to natural carotenoid compounds. For example, synthetic lycopene may be up to 25% 5-cis, 1% 9-cis, 1% 13-cis, and 3% other cis isomers, whilst lycopene produced by tomatoes may be 3-5% 5-cis, 0-1% 9-cis, 1% 13-cis, and <1% other cis isomers. Since cis-lycopene has increased bioavailability relative to trans-lycopene, synthetic lycopene is preferred in some embodiments.

Derivatives of carotenoids as described above may be produced by chemical synthesis analogous to the synthesis described above or by chemical modification of natural carotenoids extracted from plant material.

A food product as described herein may contain a single carotenoid compound (e.g. lycopene) or more than one carotenoid compound (e.g. lycopene and beta-carotene). Typically, each carotenoid compound will be present in a range of different isomeric forms.

The food product may be produced by admixing or blending fat compounds, such as buttermilk, and optionally one or more other ingredients, with the carotenoid compound under conditions which allow the carotenoid compound to incorporate into the matrix of the food product.

The invention also provides for a method of producing a food product, such as a food product of the invention, which comprises adding a carotenoid during production of the food product. For instance, the method may comprise adding the carotenoid during preparation of the food product. In one instance, the method may comprise blending and/or mixing the carotenoid, or composition comprising the carotenoid, with a butter, margarine, oil or cooking fat, including any of the types of butter, margarine or oils mentioned herein. The method may comprise blending or mixing a carotenoid, or composition comprising the carotenoid, with milk or cream.

The invention also provides a method comprising cooking a foodstuff, where the method comprises adding a carotenoid or carotenoid composition, during preparation of the product to be cooked, then cooking the product.

Products of the invention may also contain other ingredients such as flavourings, emulsifiers, colourings and/or preservatives.

Other ingredients may include sugar, vanilla, milk, milk powder, emulsifying agents, such as soy lecithin or polyglycerol polyricinoleate (PGPR; E476), whey or potato peptides and/or proteins, soy products, such as soy proteins, soy extracts and/or soy isoflavones, vegetable oils or animal fats, nut-based products, such as nut powders and nut extract, starch and polysaccharides.

The fat compounds may be in a dry, liquid, aerosol, frozen or melted form for admixing or blending with the carotenoid compound. For example, fat compounds for blending may be in liquid form (e.g. melted butter or margarine). In some preferred embodiments, the fat compounds and the carotenoid compound are in mixable forms and have the same or similar viscosities.

Suitable methods of mixing and blending, including mechanical blending, are well-known in the art.

Food products as described herein are shown to have an unexpected effect on levels of blood cholesterol, low density lipoprotein, triglycerides and/or other lipids or lipid particles, such as LDL particles, in an individual.

Aspects of the invention provide a food product as described above for use in reducing blood levels of cholesterol, low density lipoprotein, triglycerides and/or other lipids or lipid particles, such as LDL particles, in an individual and a method of reducing blood levels of cholesterol, low density lipoprotein, triglycerides and/or other lipids or lipid particles, such as LDL particles, in an individual comprising administering a food product described above to the individual.

Another aspect of the invention provides the use of a carotenoid compound and one or more fat bean products, as described above, in the manufacture of a food product for use in reducing blood levels of cholesterol, low density lipoprotein, triglycerides and/or other lipids or lipid particles, such as LDL particles, in an individual.

This may be useful in the treatment or prevention of cardio- and cerebro-vascular disorders, or Metabolic Syndrome, high blood pressure, pre-diabetes and type II diabetes, being overweight (e.g. BMI>25) and obesity (e.g. BMI>30).

The invention may be employed, for instance, with any of those subjects. The products of the invention may be used in dieting. The invention also provides a method of dieting comprising consuming a product of the invention as part of the diet.

An individual is preferably a human, though use in animals is also possible. The individual may have normal blood levels of cholesterol, LDL and/or triglycerides or elevated blood levels of cholesterol, LDL and/or triglycerides. In some instances, the subject may have a total serum cholesterol of more than 200 mg/dL, for instance more than 210 mg/dL. In some cases a subject may additionally, or alternatively have, triglyceride levels above 150 mg/dL. In some cases, the subject may be apparently healthy, but identified as having such elevated levels of cholesterol and/or triglycerides, in other instances the subject may have a history of heart disease and/or atherosclerosis. The subject may be overweight and may be obese. The subject may be one taking statins, aspirin and/or blood pressure reducing medication. The subject may be one on a diet.

Methods of measuring levels of cholesterol, LDL, triglycerides and other lipids in an individual are well-known in the art.

In some cases, the subject may be apparently healthy, but be identified as having such elevated levels of cholesterol and/or triglycerides, in other instances the subject may have a history of heart disease and/or atherosclerosis. The subject may be overweight and may be obese. The subject may be one taking statins, aspirin and/or blood pressure reducing medication. The subject may be one on a diet.

Methods of measuring levels of cholesterol, LDL, triglycerides and other lipids in an individual are well-known in the art.

In some embodiments, the individual may be at risk of, or suffering from, a cardio- or cerebro-vascular disorders, such as coronary heart disease, metabolic syndrome, high blood pressure, pre-diabetes and type II diabetes, being overweight (e.g. BMI>25) or obesity (e.g. BMI>30). The subject may have had a heart attack. The subject may have had a stoke.

The food products may also be useful in reducing inflammation; reducing anti-inflammatory oxidative damage; increasing antioxidant activity and/or reducing or delaying symptoms of aging in an individual. The invention may be used to reduce the visible signs of aging. Food products as described herein are also shown to reduce levels of markers of inflammatory oxidative damage in an individual. The food products may also be useful in reducing inflammation; reducing anti-inflammatory oxidative damage; increasing antioxidant activity and/or reducing or delaying symptoms of aging in an individual.

For example, daily dose of 0.1 mg to 100 mg of carotenoid compound, such as lycopene, preferably 0.5 to 50 mg, may be administered to the individual.

In some embodiments, a suitable individual may be a mature or elderly individual, for example at least 50 years old.

Food products as described herein may also be useful in providing nutrition to an individual.

For example, food products may be useful as sports nutrition products or in providing nutrition to mature or elderly individuals (e.g. >50 years old) or individuals undergoing body mass control or reduction, i.e. for "slimming" purposes. In some cases, the individual may be at least 50, 60, 65, 70, 75 or more years old or be of an age in the range defined by any of those two values.

In other examples, food products may be useful in providing nutrition to individual having or recovering from a clinical condition. For example, food products described herein may be useful in the nutrition of an individual recovering from injury, operation, or trauma; an individual having or recovering from chemo- or radio-therapy; or an individual having or at risk of Metabolic Syndrome, obesity, diabetes II, atherosclerosis and their clinical complications.

Food products as described herein may also be useful in the treatment or prevention of cardio- and cerebro-vascular disorders, hypertension, metabolic syndrome, high blood pressure, pre-diabetes and type II diabetes, being overweight (e.g. BMI>25), obesity (e.g. BMI>30) or other medical conditions such as anaemia, rheumatism, rheumatoid arthritis, non-rheumatoid arthritis, prostate or testes malfunctions, erectile dysfunctions, loss of libido, cellulite, sarcopenia and cachexia.

In some instances, the subject the invention is applied to may have an auto-immune disease; an allergic condition; hypertension; atherosclerosis; cardio pathologies, such as Coronary Heart Disease; vascular pathologies, such as endocarditis, myocarditis, heart failure, heart valve disease, arrhythmias, atherosclerosis, hypertension, vasculitis, endarteritis, varicose veins, endophlebitis, endothelial damage; cerebral pathologies; obesity; diabetes type 2; cancer, sarcopenia; metabolic dysfunction; Metabolic Syndrome; cellulite and aging tissue degradation; gastritis; stomach or duodenum ulcers; or arthritis; or dermatitis, psoriasis, acne, chronic skin ulcerations, or other age-related or not skin conditions, including skin and other tissues burns and wounds; sport, trauma, operation and other injuries; cachexia, side-effects of chemotherapies and radiation treatment, or radiation exposure; the subject may be at risk of such a condition.

The invention may also be used to treat conditions where increased oxygen transport may be beneficial. For instance, a subject with a respiratory disorder such as emphysema, COPD, cystic fibrosis, asthma, or ARDS. The subject may have reduced lung function, for instance due to lung damage or lung cancer. In one instance, the subject may be a smoker.

The invention may also be employed to help treat inflammatory or autoimmune disorders, for instance arthritis, inflammatory bowel disease and atherosclerosis.

The invention may also be used to treat impairment of tissue oxygenation, for instance due to reduction of blood supply due to circulatory dysfunction or circulatory disease. The subject may have had an injury, disease or disorder causing reduced blood flow, for instance one that results from blood flow to an organ and/or tissue being reduced or cut-off.

The invention may be used to increase tissue oxygenation and treat circulatory disease. In one instance the circulatory disorder may be due to traumatic, compressive, occlusive, tumors/malformations and/or vasospastic reduction in oxygenation. The subject may have atherosclerosis resulting in reduced tissue oxygenation or DVT. The subject may be one with angina, such as angina pectoris, acute coronary syndrome, or had a myocardial infraction. The invention may also be used to treat individuals with reduced tissue inflammation due to ongoing inflammatory conditions or processes in the tissue, such as any of those referred to herein.

In one preferred instance, a foodstuff of the invention may be provided with packaging and/or wrapping. Such packaging/wrapping may indicate the benefits of the invention. The packaging/wrapping may indicate the benefits of the product in slimming, decreasing cholesterol, and/or triglyceride levels. The packaging may refer to treating or ameliorating any of the conditions mentioned herein. The packaging may be a sachet, for instance where the product is to be made up as a beverage.

Another aspect of the invention provides a nutracosmetic formulation comprising one or more fat bean products and a carotenoid compound. Suitable fat bean products and carotenoid compounds are described in more detail above.

A nutracosmetic formulation which comprises one or more fat bean products and a carotenoid compound as defined above, may further comprise one or more cosmetically or nutritionally acceptable carriers, adjuvants, excipients, sweeteners, diluents, fillers, buffers, stabilisers, preservatives, colourings, lubricants, or other materials well known to those skilled in the art.

The term "nutraceutically acceptable" as used herein pertains to compounds, materials, compositions, and/or dosage forms which are in common or widespread usage in food and dietary products and are generally considered non-toxic, for example, compounds may have the US FDA designation "GRAS" (Generally Recognised as Safe), or equivalent food additive status in other jurisdictions.

Nutracosmetic formulations are generally intended for oral administration and may be formulated accordingly.

Nutracosmetic formulations may be useful in improving the appearance of an individual or in reducing, delaying or masking visual signs of aging in an individual.

The invention may be administered to treat, ameliorate, prevent, or reduce the severity of symptoms in any of the conditions referred to herein. In one instance, the invention is administered prophylactically to help prevent the onset of any of the conditions mentioned herein. The invention may result in reduction of any of the parameters discussed herein, it may, for instance, reduce cholesterol, triglyceride, inflammatory damage, weight or body fat.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

In instances herein where the terms "comprises" or "comprising" are used, the invention may also provide what is described when it "consists essentially of" or "consisting of" the specified constituents.

Unless context dictates otherwise, the descriptions and definitions of the features set out above are not limited to any particular aspect or embodiment of the invention and apply equally to all aspects and embodiments which are described.

The following is a list of some further numbered embodiments of the invention:

(1) A food product comprising one or more fats or oils and an isolated carotenoid compound.

(2) A food product according to (1) which comprises a homogenous matrix containing the fats or oils and the carotenoid compound.

(3) A food product according to (1) or (2) wherein the fats comprise one or more of animal or bird fats, or vegetable or other plant fats or oils, fungi, algae or bacteria fats, synthetic fats.

(4). A food product according to any one of (1) to (3) where the one or more fats or oils are in the form of a food matrix, said matrix incorporating the carotenoid compound.

(5) A food product according to any one of (1) to (4) which comprises 0.001 to 10 mg of carotenoid compound per gram of food product.

(6) A food product according to any one of (1) to (5) the preceding claims wherein the carotenoid compound is a lycopene compound.

(7) A food product according to any one of (1) to (6) wherein the carotenoid compound is comprised in a carotenoid-rich product, such as tomato or other fruit, vegetable or plant paste, sauce, concentrate, oleoresin, fraction or extract, synthetic or purified molecules.

(8) A food product according to any one of (1) to (6) wherein the carotenoid compound is comprised in a carotenoid rich fruit, vegetable or other plant, or fungus, yeast, algae or bacterium, synthetic or purified molecules.

(9) A food product according to any one of (1) to (8) wherein the lycopene compound is lycopene.

(10) A food product according to any one of (1) to (9) wherein the food product is produced by admixing or blending together the fats, the carotenoid compound and optionally one or more additional ingredients.

(11) A food product according to (10) wherein the fats or oils are admixed or blended, or sonicated, or sprayed-dried, or embedded by other means together with the carotenoid compound in a dry, liquid, aerosol, frozen or melted form.

(12) A food product according to any one of (1) to (11) wherein the food product is a foodstuff.

(13) A food product according to (12) wherein the foodstuff is bread, flour, cereal, biscuit, pastry, shortening, spread, filling, paste, sauce, mousse, cream, or yogurt.

(14) A food product according to (12) wherein the foodstuff comprises butterfat.

(15) A food product according to (14) wherein the foodstuff is cheese, butter, milk, cream or ice cream.

(16) A food product according to (12) wherein the foodstuff is margarine or lard.

(17) A food product according to (1) to (11) wherein the food product is a beverage.

(18) A food product according to any one of (1) to (11) wherein the food product is a dietary supplement, nutracosmetic or nutraceutical product.

(19) A food product according to any one of (1) to (18) for use in reducing elevated levels of cholesterol, LDL and/or triglyceride in an individual.

(20) A food product according to any one of (1) to (19) for use in reducing subclinical or clinical inflammation; reducing anti-inflammatory oxidative damage; increasing plasma molecular oxygen transport, microcirculation and tissue oxygen saturation, reducing already developed liver (micro-) damage and liver steatosis, liver and other organs, including peripheral, tissue hypoxia or ischaemia; increasing antioxidant activity and/or reducing or delaying symptoms of aging in an individual.

(21) A food product according to any one of (1) to (20) for use in reducing postprandial cholesterol- and triglyceride-aemias, reducing size of chylomicrons and increasing rate of their clearance, reducing postprandial inflammatory and oxidative stress, reducing postprandial or other liver (micro-) damage and liver steatosis, liver and other organs, including peripheral tissue hypoxia or ischaemia, or delaying of above mentioned symptoms of fat, or excessive, or imbalance food intake in an individual.

(22) A food product according to any one of (1) to (21) for use in the nutrition of an individual.

(23) A food product for use according to (22) wherein the individual is mature or elderly.

(24) A food product for use according to any one of (19) to (23) wherein the individual is undergoing body mass control or body mass reduction.

(25) A food product for use according to any one of (19) to (23) wherein the individual is suffering from; at risk of suffering from; or recovering from a clinical condition.

(26) A food product for use according to (25) wherein the individual is recovering from injury, operation, or trauma or undergoing or recovering from chemo- or radio-therapy; or having or being at risk of having Metabolic Syndrome, obesity, diabetes II, atherosclerosis and clinical complications thereof.

(27) A food product for use according to any one of (1) to (20) for the treatment of a clinical condition.

(28) A food product for use according to (27) wherein the clinical condition is a cerebro-vascular disorder, cardio-vascular disorder, hypertension, metabolic syndrome, high blood pressure, pre-diabetes, type II diabetes, being overweight (e.g. BMI>25), obesity (e.g. BMI>30), anaemia, rheumatism, rheumatoid arthritis, non-rheumatoid arthritis, prostate or testes malfunction, erectile dysfunction, loss of libido, cellulite, age-related functions of liver, skin and other organs, sarcopenia and cachexia.

(29) A method of improving the appearance of an individual comprising administering a nutracosmetic formulation according to any one of (1) to (18) to the individual.

(30) A method of reducing or delaying visible signs of aging and performance in an individual comprising administering a nutracosmetic formulation according to any one of (1) to (18) to the individual.

(31) A method of reducing elevated levels of cholesterol, LDL and/or triglyceride in the blood of an individual comprising administering a food product according to any one of (1) to (18) to an individual in need thereof.

(32) A method of reducing subclinical or clinical inflammation; reducing anti-inflammatory oxidative damage; increasing plasma molecular oxygen transport, microcirculation and tissue oxygen saturation, reducing already developed liver (micro-) damage and liver steatosis, liver and other organs, including peripheral, tissue hypoxia or ischaemia; increasing antioxidant activity and/or reducing or delaying symptoms of ageing in an individual; comprising administering a food product according to any one of (1) to (18) to an individual in need thereof.

(33) A method of reducing postprandial cholesterol- and triglyceride-aemias, reducing size of chylomicrons and increasing rate of their clearance, reducing postprandial inflammatory and oxidative stress, reducing postprandial or other liver (micro-) damage and liver steatosis, liver and other organs, including peripheral tissue hypoxia or ischaemia, or delaying of above mentioned symptoms of fat, or excessive, or imbalance food intake in an individual; comprising administering a food product according to any one of (1) to (16) to an individual in need thereof.

(34) A method of providing nutrition to an individual comprising administering a food product according to any one of (1) to (18) to an individual in need thereof.

(35) A method according to (34) wherein the individual is mature or elderly.

(36) A method according to any one of (31) to (35) wherein the individual is undergoing body mass control or body mass reduction.

(37) A method according to any one of (31) to (36) wherein the individual is suffering from; at risk of suffering from; or recovering from a clinical condition.

(38) A method according to (37) wherein the individual is recovering from injury, operation, or trauma or undergoing or recovering from chemo- or radio-therapy; or having or being at risk of having Metabolic Syndrome, obesity, type II diabetes, atherosclerosis and clinical complications thereof.

(39) A method of treatment of a clinical condition comprising administering a food product according to any one of (1) to (18) to an individual in need thereof.

(40) A method of treatment according to (38) wherein the clinical condition is cerebro-vascular disorder, cardio-vascular disorder, hypertension, metabolic syndrome, high blood pressure, pre-diabetes, type II diabetes, being overweight (e.g. BMI>25), obesity (e.g. BMI>30), anaemia, rheumatism, rheumatoid arthritis, non-rheumatoid arthritis, prostate or testes malfunction, erectile dysfunction, loss of libido, cellulite, age-related functions of liver, skin and other organs, sarcopenia or cachexia.

Certain aspects and embodiments of the invention will now be illustrated by way of example and with reference to the tables described below.

Table 1 shows the effect of lycopene on lipid parameters, and markers of IOD and inflammation in CHD patients.

Table 1 shows the effect of 30 g butter on lipid parameters, and markers of IOD and inflammation in CHD patients.

Table 3 shows the effect of 30 g of L-butter on lipid parameters, and markers of IOD and inflammation in CHD patients.

Clinically Healthy Volunteers with Hypercholesterolaemia
Lipid-Lowering Butter (L-Butter)

Commercially available butter (President, Lactalis) was melted at 40° C. The melted butter was blended with tomato oleoresin, containing 15% of lycopene (Lyc-O-Mato), in the ratio of 7 mg of oleoresin to 30 g of the butter in a thermo-controlled mixer. The mixture was blended for 10 minutes and cooled down to the room temperature. The butter was then divided into daily 30 g portions. Butter was stored at 4° C. until use. Freshly made batches of the L-Butter were made weekly.

Each portion of 30 g butter contained 47.1 mg of tomato oleoresin or about 7 mg of lycopene.

Control Samples of Butter

The melting and mixing procedures were performed as described above using the same commercially available butter, but instead of tomato oleoresin, sunflower oil (Flora™) was used.

Lycopene 47.1 mg of tomato oleoresin was pre-dissolved in ethanol and mixed with Whey Protein as described in Richelle et al (2002) J. Nutr 132 404-408, WO01/091588 and US2002/01072992. Then the mixture was placed into gelatine capsules.

All products were kept in cool dry, protected from light conditions.

Clinical Groups 18 clinically healthy volunteers, 9 males and 9 females, age 45-69, were recruited for this study.

Main inclusion criteria were:
 elevated total serum cholesterol above 200 mg/dL and/or triglycerides above 150 mg/dL,
 all patients were naive for any lipid-lowering medications,
 willing participate in the study.

Secondary inclusion criteria were:
  positive blood markers of inflammatory oxidative damage, IOD, ≥20-30 μM MDA
  positive blood on an antibody inflammatory marker, Px-IgG≥0.250-0.300 U/ml All patients were randomised and divided into three equal groups of 6 volunteers each. Two groups receiving butter were blinded; the group receiving lycopene preparation along was open labelled.

All blood samples were coded. Their lab analysis and reading of the results were blinded. The period of the trial was 4 weeks.

Results

The results of the ongoing trial are presented in the tables 1 to 3 below. It was observed that after one week of administration of 7 mg of lycopene, there were not any changes in any patients on their levels of elevated cholesterol, triglycerides and markers of oxidative damage or inflammation (table 1). In the group where patients were taking 30 g of the control butter in addition to their regular diet, by the end of the first week there was a significant increase in the serum total cholesterol, by 39 mg/dL, in its LDL fraction by 31 mg/dL and in triglycerides, by 14 mg/dL (table 2). By the end of week 2 these parameters were noticeably reduced but have not reached their baseline level yet.

In the group, where patients were taking 30 g of L-Butter, after first week there was a significant reduction in the main serum lipid fractions—total cholesterol was reduced by 35 mg/dL, and triglyceride by 13 mg/dL. This trend continued further during the second week (table 3). A trend in the reduction of serum inflammatory markers was also observed, indicating that this product has not only lipid-lowering properties but an anti-inflammatory as well.

The results described herein show the unusual and unexpected outcome of the blending of carotenoids such as lycopene with fat-based products. Not only is fat butter prevented from contributing to the rise of blood lipids, but the blend actively reduces lipids which are already at an elevated level. Such results are counter-intuitive as the consumption of high fat butter would be expected to contribute to a substantial rise in cholesterol. In particular, These results are unexpected because the benefit of adding any ingredient with additional health value to butter or other fat containing products would be expected to be outweighed by the potential harmful consequences of consuming increased amounts of fats.

The altered properties of the carotenoid containing foodstuffs are not nutritional—butter and fat containing products still have the same content of fatty acids and other essential lipids. However, incorporating carotenoids, such as lycopene, into these products' matrixes, whilst not wanting to be bound by any particular theory, seems to significantly improve their metabolism. This results not only in the prevention of the hyper-lipidaemia, which can be developed as result of the consumption of these products, but also in the reduction blood lipids in those people who had them elevated even before they start to consume the 'Lycopene-Butter'. The incorporation of high carotenoids does not change the taste or physical properties of the fat containing food products, for example spread-ability of the butter.

The invention concerns the unusual, and unexpected outcome of the blending of fat-containing products and carotenoids. This blending not only prevents butter or other fat containing products from contributing to increases in blood lipids, but also actively reduces plasma lipids such as total cholesterol, its LDL fraction and triglycerides, which are already at an elevated level.

In other words, the invention described herein not only makes fat products, such as butter, "safer" from the health impact point of view, but may also makes them useful as a proactive interventional product for slimming, lipid-lowering purposes and anti-aging purposes, and for prevention and help in management of metabolic, pre-diabetes, cardiovascular and other conditions.

New Opportunities to Control Lipid Metabolism, Inflammation and Tissue Oxygenation The results presented here open a possible new mechanisms and new ways not only to control already developed changes in the lipid metabolism but also to prevent these changes. These results also provide a prototype of the development of new ways to control subclinical and maybe other forms of inflammation and/or boosting transport of the plasma molecular oxygen, which could be useful to restore tissue oxygen saturation which could be important in many clinical conditions and to delay ageing.

Unexpected Benefits to the Health and Industry

The results described herein are unexpected because the benefit of adding any ingredient with additional health value to fat/oil product would be expected to be outweighed by the potential harmful consequences of consuming increased amounts of this high-fat food product. Reducing fat content in food products is the standard way to minimise their fat load to the body. However these results described herein show the unusual and unexpected outcome of the blending of carotenoids such as lycopene with fat/oil products. In other words, the invention described herein not only makes fat/oil products, such as butter, "safer" from the health impact point of view, but may also make it useful as a proactive interventional product for slimming, lipid-lowering purposes and anti-aging purposes, and for prevention and help in management of metabolic, pre-diabetes, cardiovascular and other conditions.

TABLE 1

| | | | | | | | | | | |
|---|---|---|---|---|---|---|---|---|---|---|
| | | | Lycopene | | | | | | | |
| ID | Age | IOD μM MDA | Px-IgG U/ml | TC mg/dL | TG mg/dL | HDL mg/dL | LDL mg/dL | GL mmol/L | AST U/L | ALT U/L |
| | | | | Baseline | | | | | | |
| 13 | 48 | 101 | 0.765 | 225 | 161 | 39 | 153 | 6.5 | 44 | 25 |
| 14 | 69 | 162 | 0.698 | 231 | 150 | 42 | 159 | 5.6 | 45 | 36 |
| 15 | 54 | 79 | 0.811 | 204 | 134 | 41 | 135 | 3.8 | 34 | 24 |
| 16 | 49 | 95 | 0.803 | 219 | 126 | 44 | 161 | 4.4 | 27 | 35 |
| 17 | 66 | 83 | 0.751 | 243 | 165 | 37 | 186 | 5.9 | 49 | 29 |
| 18 | 53 | 49 | 0.743 | 210 | 157 | 40 | 147 | 6.1 | 25 | 26 |
| | 56.5 | 95 | 0.762 | 222 | 149 | 40.5 | 157 | 5.4 | 37.3 | 29.2 |

TABLE 1-continued

Lycopene

| ID | Age | IOD μM MDA | Px-IgG U/ml | TC mg/dL | TG mg/dL | HDL mg/dL | LDL mg/dL | GL mmol/L | AST U/L | ALT U/L |
|---|---|---|---|---|---|---|---|---|---|---|
| Week 1 |
| 13 | 48 | 99 | 0.823 | 224 | 160 | 39 | 153 | 6.4 | 47 | 31 |
| 14 | 69 | 158 | 0.746 | 231 | 152 | 42 | 160 | 5.7 | 46 | 33 |
| 15 | 54 | 85 | 0.809 | 205 | 137 | 40 | 134 | 4.9 | 36 | 29 |
| 16 | 49 | 94 | 0.867 | 217 | 130 | 43 | 160 | 3.6 | 31 | 34 |
| 17 | 66 | 81 | 0.851 | 241 | 164 | 38 | 185 | 5.1 | 44 | 33 |
| 18 | 53 | 57 | 0.839 | 209 | 159 | 40 | 149 | 6.1 | 34 | 29 |
|  |  | 96 | 0.823 | 221 | 150 | 40.3 | 157 | 5.3 | 39.7 | 31.5 |
| Week 2 |
| 13 | 48 | 95 | 0.812 | 223 | 159 | 39 | 152 | 6.6 | 43 | 29 |
| 14 | 69 | 139 | 0.809 | 230 | 151 | 41 | 158 | 5.2 | 42 | 31 |
| 15 | 54 | 84 | 0.815 | 208 | 138 | 40 | 133 | 5.4 | 31 | 28 |
| 16 | 49 | 91 | 0.844 | 216 | 132 | 42 | 159 | 4.1 | 38 | 32 |
| 17 | 66 | 75 | 0.830 | 239 | 162 | 39 | 183 | 3.9 | 41 | 31 |
| 18 | 53 | 68 | 0.799 | 208 | 158 | 41 | 150 | 6 | 30 | 34 |
|  |  | 92 | 0.818 | 221 | 150 | 40.3 | 156 | 5.2 | 37.5 | 30.8 |

TABLE 2

Butter

| ID | Age | IOD μM MDA | Px-IgG U/ml | TC mg/dL | TG mg/dL | HDL mg/dL | LDL mg/dL | GL mmol/L | AST U/L | ALT U/L |
|---|---|---|---|---|---|---|---|---|---|---|
| Baseline |
| 25 | 53 | 106 | 0.788 | 215 | 159 | 43 | 155 | 6.1 | 28 | 29 |
| 26 | 64 | 77 | 0.834 | 242 | 196 | 38 | 189 | 5.9 | 45 | 36 |
| 27 | 48 | 114 | 0.752 | 229 | 177 | 41 | 161 | 4.3 | 31 | 37 |
| 28 | 57 | 151 | 0.539 | 209 | 138 | 40 | 142 | 3.5 | 27 | 21 |
| 29 | 69 | 48 | 0.741 | 235 | 174 | 42 | 163 | 6.4 | 29 | 26 |
| 30 | 51 | 93 | 0.65 | 219 | 156 | 39 | 152 | 5.5 | 32 | 29 |
|  | 57 | 98.2 | 0.717 | 225 | 167 | 40.5 | 160 | 5.3 | 32 | 29.7 |
| Week 1 |
| 25 | 53 | 112 | 0.942 | 258 | 172 | 42 | 195 | 5.9 | 32 | 33 |
| 26 | 64 | 89 | 0.811 | 275 | 205 | 38 | 211 | 6 | 53 | 37 |
| 27 | 48 | 108 | 0.698 | 269 | 191 | 42 | 194 | 5.4 | 37 | 38 |
| 28 | 57 | 167 | 0.745 | 247 | 158 | 41 | 167 | 5.2 | 31 | 25 |
| 29 | 69 | 75 | 0.791 | 271 | 183 | 41 | 192 | 6.6 | 39 | 31 |
| 30 | 51 | 104 | 0.882 | 266 | 175 | 39 | 187 | 5.9 | 29 | 27 |
|  |  | 109 | 0.812 | 264 | 181 | 40.5 | 191 | 5.8 | 36.8 | 31.8 |
| Week 2 |
| 25 | 53 | 104 | 0.745 | 231 | 163 | 42 | 164 | 6 | 29 | 32 |
| 26 | 64 | 65 | 0.709 | 229 | 185 | 38 | 193 | 5.8 | 44 | 35 |
| 27 | 48 | 96 | 0.589 | 243 | 163 | 41 | 171 | 4.9 | 35 | 30 |
| 28 | 57 | 142 | 0.698 | 222 | 150 | 42 | 149 | 4.5 | 29 | 26 |
| 29 | 69 | 93 | 0.732 | 254 | 179 | 41 | 175 | 6.4 | 37 | 29 |
| 30 | 51 | 101 | 0.809 | 265 | 164 | 39 | 160 | 5.1 | 31 | 24 |
|  |  | 100 | 0.714 | 241 | 167 | 40.5 | 169 | 5.45 | 34.2 | 29.3 |

TABLE 3

L-Butter

| ID | Age | IOD μM MDA | Px-IgG U/ml | TC mg/dL | TG mg/dL | HDL mg/dL | LDL mg/dL | GL mmol/L | AST U/L | ALT U/L |
|---|---|---|---|---|---|---|---|---|---|---|
| Baseline |
| 19 | 56 | 117 | 0.78 | 229 | 83 | 50 | 119 | 5.3 | 29 | 28 |
| 20 | 55 | 56 | 0.876 | 200 | 99 | 45 | 129 | 4.8 | 23 | 33 |
| 21 | 63 | 104 | 0.817 | 232 | 176 | 40 | 156 | 4.6 | 28 | 82 |
| 22 | 59 | 71 | 0.745 | 203 | 111 | 48 | 130 | 4.7 | 33 | 43 |
| 23 | 45 | 110 | 0.936 | 222 | 200 | 40 | 160 | 5.9 | 16 | 18 |
| 24 | 54 | 139 | 0.892 | 241 | 189 | 38 | 183 | 4.8 | 32 | 31 |
|  | 55 | 99.5 | 0.841 | 221 | 143 | 43.5 | 146 | 5.02 | 26.8 | 39.2 |

TABLE 3-continued

| | | | | | L-Butter | | | | | |
|---|---|---|---|---|---|---|---|---|---|---|
| ID | Age | IOD µM MDA | Px-IgG U/ml | TC mg/dL | TG mg/dL | HDL mg/dL | LDL mg/dL | GL mmol/L | AST U/L | ALT U/L |
| | | | | | Week 1 | | | | | |
| 19 | 56 | 84 | 0.671 | 216 | 82 | 50 | 119 | 4.6 | 29 | 29 |
| 20 | 55 | 36 | 0.752 | 154 | 65 | 46 | 127 | 4.8 | 23 | 33 |
| 21 | 63 | 72 | 0.721 | 180 | 170 | 40 | 150 | 4.4 | 26 | 86 |
| 22 | 59 | 47 | 0.731 | 200 | 90 | 48 | 127 | 4.2 | 30 | 36 |
| 23 | 45 | 91 | 0.783 | 173 | 197 | 40 | 157 | 5.7 | 16 | 17 |
| 24 | 54 | 102 | 0.719 | 191 | 175 | 39 | 176 | 5.1 | 29 | 23 |
| | | 72 | 0.729 | 186 | 130 | 43.8 | 143 | 4.8 | 25.5 | 37.3 |
| | | | | | Week 2 | | | | | |
| 19 | 56 | 53 | 0.431 | 206 | 83 | 50 | 118 | 4.3 | 27 | 29 |
| 20 | 55 | 29 | 0.259 | 158 | 65 | 46 | 126 | 4.1 | 24 | 31 |
| 21 | 63 | 57 | 0.572 | 166 | 138 | 42 | 146 | 4.6 | 24 | 80 |
| 22 | 59 | 32 | 0.317 | 200 | 91 | 48 | 127 | 3.9 | 30 | 33 |
| 23 | 45 | 69 | 0.631 | 146 | 189 | 41 | 150 | 4.5 | 19 | 17 |
| 24 | 54 | 84 | 0.503 | 180 | 142 | 40 | 131 | 4.5 | 22 | 25 |
| | | 54 | 0.452 | 176 | 118 | 44.5 | 133 | 4.5 | 24.3 | 35.8 |

The invention claimed is:

1. A method of reducing elevated levels of cholesterol, low density lipoproteins and/or triglycerides in the blood of a human in need thereof comprising administering to the human in need thereof a therapeutically effective amount of a butter having an isolated carotenoid or carotenoids selected from the group consisting of lycopene, lutein and zeaxanthin in the matrix of the butter.

2. The method of claim 1, wherein the butter comprises isolated lutein.

3. The method of claim 1, wherein the butter comprises isolated lycopene.

4. The method of claim 1, wherein the butter comprises isolated zeaxanthin.

5. The method of claim 1, wherein the human is overweight or obese.

6. The method of claim 1, wherein the human has type 2 diabetes, atherosclerosis or hypertension.

* * * * *